United States Patent
Li et al.

(10) Patent No.: US 11,654,272 B2
(45) Date of Patent: May 23, 2023

(54) ONE-TIME PRIMING IV INFUSION EXTENSION SET

(71) Applicant: CareFusion 303, Inc., San Diego, CA (US)

(72) Inventors: Jiagui Li, Shanghai (CN); Rongjie Liang, Suzhou (CN); George Michael Mansour, Diamond Bar, CA (US)

(73) Assignee: CareFusion 303, Inc., San Diego, CA (US)

( * ) Notice: Subject to any disclaimer, the term of this patent is extended or adjusted under 35 U.S.C. 154(b) by 852 days.

(21) Appl. No.: 16/578,072

(22) Filed: Sep. 20, 2019

(65) Prior Publication Data

US 2021/0085949 A1    Mar. 25, 2021

(51) Int. Cl.
    *A61M 39/10*    (2006.01)
(52) U.S. Cl.
    CPC ... *A61M 39/105* (2013.01); *A61M 2039/1077* (2013.01); *A61M 2039/1083* (2013.01)
(58) Field of Classification Search
    CPC .......... A61M 39/105; A61M 2039/177; A61M 2039/1083; A61M 2005/1402; A61M 5/1407; A61M 5/1413
    See application file for complete search history.

(56) References Cited

U.S. PATENT DOCUMENTS

| | | | |
|---|---|---|---|
| 4,257,416 A * | 3/1981 | Prager | A61M 5/1408 604/83 |
| 9,925,329 B2 | 3/2018 | Reichert et al. | |
| 2008/0200904 A1* | 8/2008 | Cluff | A61M 25/00 604/537 |
| 2015/0080814 A1 | 3/2015 | Lambert et al. | |

FOREIGN PATENT DOCUMENTS

| | | |
|---|---|---|
| AU | 2011248902 B2 | 9/2015 |
| WO | WO-0141835 A2 | 6/2001 |

OTHER PUBLICATIONS

Carefusion. IV Sets and accessories catalog. Feb. 2013. (Year: 2013).*
International Search Report and Written Opinion for Application No. PCT/US2020/050560, dated Nov. 26, 2020, 14 pages.

* cited by examiner

*Primary Examiner* — Nathan R Price
*Assistant Examiner* — Melissa A Snyder
(74) *Attorney, Agent, or Firm* — Morgan, Lewis & Bockius LLP

(57) ABSTRACT

A multi-tubing intravenous (IV) extension set may include an outlet tubing fluidly coupled to a primary multi-tubing connector at one end and fluidly coupled to a vascular device at an opposite end, and a primary inlet tubing having a proximal end with an adapter for connection to a syringe containing a priming or a medicinal fluid, and a distal end coupled to the primary multi-tubing connector. The IV extension set may further include at least one secondary inlet tubing with a proximal end having an adapter for receiving a medicinal fluid and a distal end selectively fluidly coupled to the primary multi-tubing connector. A slide clamp may be positioned on the outlet tubing to restrict flow between the proximal and distal ends of the outlet tubing and cause priming fluid flowing into the outlet tubing via the multi-tubing connector to reverse direction into the at least one secondary inlet tubing.

19 Claims, 5 Drawing Sheets

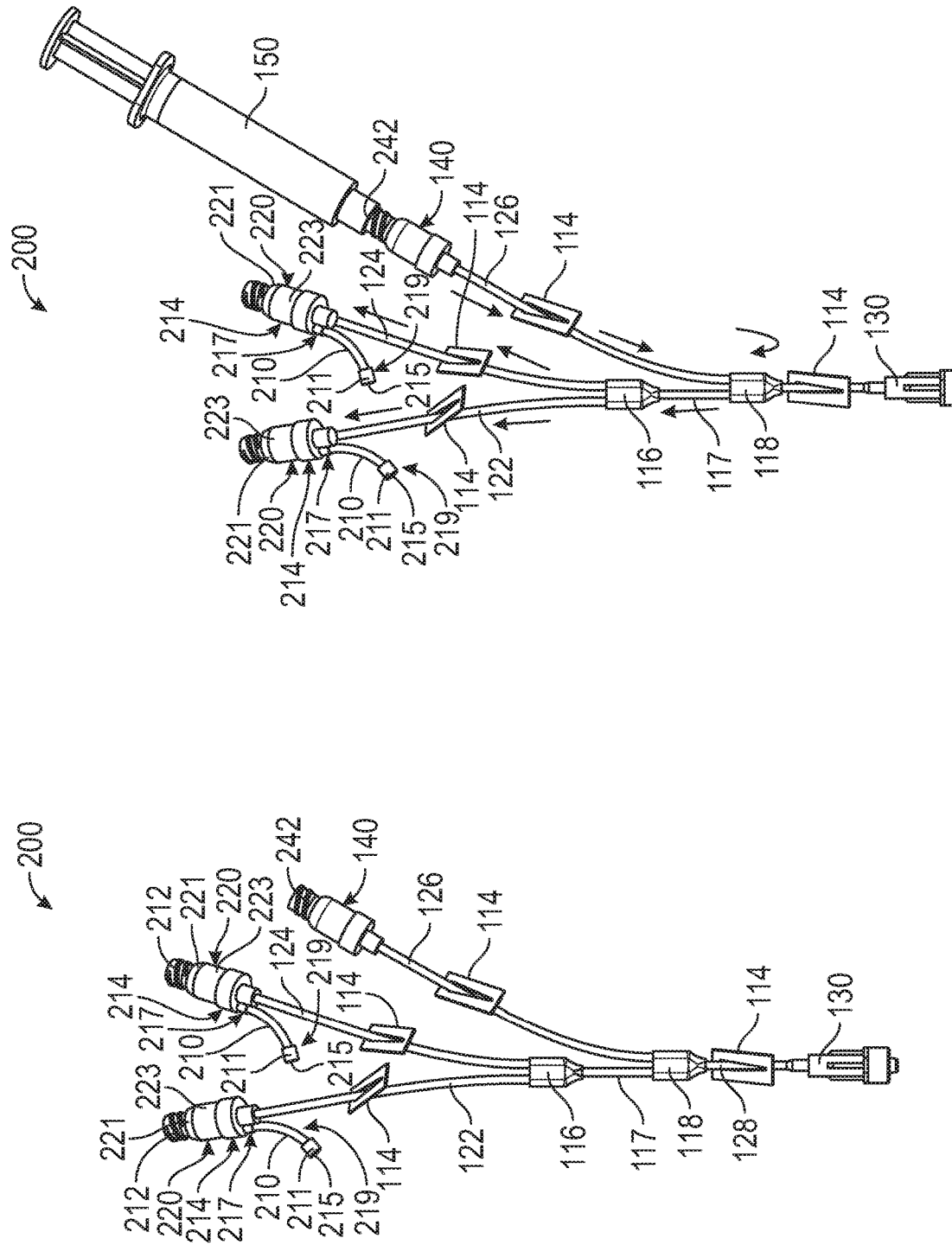

ONE-TIME PRIMING IV INFUSION EXTENSION SET

TECHNICAL FIELD

The present disclosure relates generally to IV extension sets for conveying at least two medicinal fluids to a patient independently from one another. More specifically, the present disclosure relates to an IV extension set having multiple tubing branches capable of being simultaneously primed.

BACKGROUND

Infusion IV sets are generally used in infusion therapy in order to deliver medication from a pre-filled container, e.g., an IV bag containing the desired medication, to a patient. Generally, the IV tubing is connected to a catheter which is inserted into the localized area to be treated. In some cases, there is a need to deliver multiple medications to the patient in potentially differing dosages, thereby causing the need for an IV extension set having multiple branches of tubing through which the multiple medications may be dispensed to the patient.

The description provided in the background section should not be assumed to be prior art merely because it is mentioned in or associated with the background section. The background section may include information that describes one or more aspects of the subject technology.

SUMMARY

Before infusion of medications through an IV extension set, it is desirable to prime each of the multiple tubings of the IV extension set in order to remove air from the inside of the tubing that may end up producing air bubbles in the medication to be delivered. It is desirable to remove air from inside the tubing because the air could become trapped as air bubbles in the medicinal fluid, thereby causing incorrect (e.g., too little) dosages of medication to be dispensed to the patient through the tubing.

Due to the multiple branches of tubing in many IV extension sets, for example the IV extension set illustrated in FIG. 1 described below, the practitioner connects a syringe to the adapters of each of the branches of tubing, one at a time, in order to prime each of the multiple tubings (one at a time as well). Since each of the branches of tubing of the traditional IV extension set is primed individually (one at a time), the priming process can be time consuming, especially if the extension set has several branches. As a result, the overall priming process of the some multi-tubing IV extension sets (e.g., illustrated in FIG. 1 below) may be somewhat inefficient.

Accordingly, there is a need in the field for a one-time priming IV extension set, which is configured such that a syringe having priming fluid only need be connected to one of the multiple tubing branches in order to prime all tubing branches of the extension set at once.

In accordance with various embodiments of the present disclosure, a multi-tubing intravenous (IV) extension set may include an outlet tubing, a primary inlet tuning, at least one secondary inlet tubing, and a slide clamp positioned on the outlet tubing. The outlet tubing may have a proximal end fluidly coupled to a primary multi-tubing connector and a distal end configured to be fluidly coupled to a vascular device for patient. The primary inlet tubing may have a proximal end having an adapter for connection to a syringe containing a priming or a medicinal fluid, and a distal end coupled to the primary multi-tubing connector. The at least one secondary inlet tubing may have a proximal end having an adapter for receiving a medicinal fluid and a distal end selectively fluidly coupled to the primary multi-tubing connector. The slide clamp may be configured to restrict fluid flow between the proximal and distal ends of the outlet tubing in a closed configuration to cause priming fluid flowing into the outlet tubing via the multi-tubing connector to reverse direction and flow into the at least one secondary inlet tubing via the primary multi-tubing connector.

In accordance with some embodiments, a method of simultaneously priming a plurality of tubing branches of a multi-tubing intravenous (IV) extension set having a primary inlet tubing fluidly coupled to a primary multi-tubing connector, at least one secondary inlet tubing fluidly coupled to the primary multi-tubing connector, and an outlet tubing fluidly coupling the primary multi-tubing connector to a vascular device is disclosed. The method may include connecting a syringe to an adapter of the primary inlet tubing, and pinching, bending, or otherwise folding a slide clamp positioned on the outlet tubing to block fluid flow between the proximal and distal ends of the outlet tubing. The method may further include depressing a plunger of the syringe in order to force priming fluid from the syringe downstream through the primary inlet tubing and into the outlet tubing via the primary multi-tubing connector, and reversing flow of the priming fluid to flow back upstream through the primary multi-tubing connector and into the at least one secondary inlet tubing. Air existing in the at least one secondary inlet tubing may thus be vented out of the at least one secondary inlet tubing by flowing the priming fluid therethrough.

It is to be understood that both the foregoing general description and the following detailed description are exemplary and explanatory and are intended to provide further explanation of the subject technology as claimed. It is also to be understood that other aspects may be utilized, and changes may be made without departing from the scope of the subject technology.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

FIG. 3A illustrates a one-time priming multi-tubing IV extension set that includes a hydrophobic filter in a venting cap connected to an adapter of tubing of the multiple tubing IV extension set through a venting tubing, in accordance with some embodiments of the present disclosure.

FIG. 3B illustrates a method of simultaneously priming all tubing branches of the one-time priming multi-tubing IV extension set of FIG. 3A, in accordance with some embodiments of the present disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The present invention is generally directed to tubing extension sets used in the administration of fluids to a patient that are commonly referred to as intravascular ("IV") extension sets. More particularly, various embodiments of the present disclosure are directed to a one-time priming IV extension set, which is configured such that a syringe having priming fluid only need be connected to one of the multiple tubing branches in order to prime all tubing branches of the extension set at once. Furthermore, various embodiments of the present disclosure are directed to an IV extension set having an air stop membrane that can be included within or otherwise attached to the IV extension set prevent air bubbles from accumulating in the multiple tubing branches of the IV extension set. An IV extension set according to the various embodiments of the present disclosure is used broadly herein to describe tubing sets, which may be used in the arterial, intravenous, intravascular, peritoneal, and non-vascular administration of fluid. Additionally, the IV extension sets of the various embodiments described herein may be used to administer fluids to other locations within a patient's body.

Figure 1:
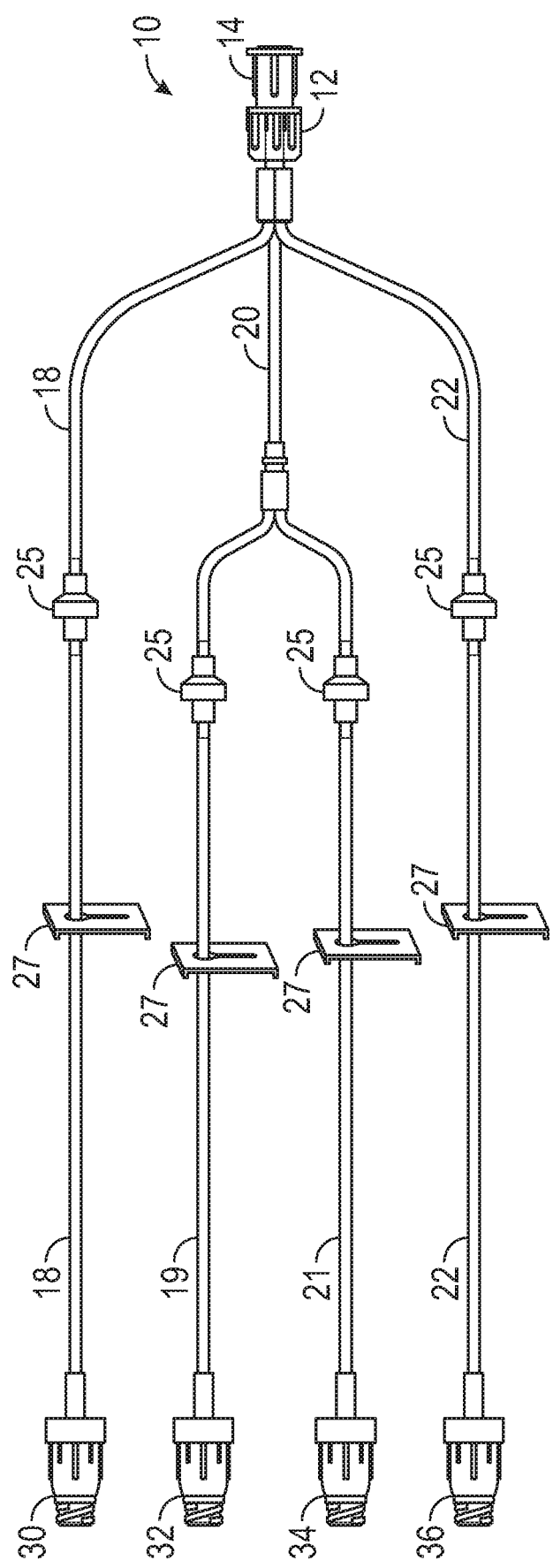
FIG. 1 illustrates a multiple tubing IV extension set, in accordance with some embodiments of the present disclosure.

One common method of administering a plurality of fluids into a patient's blood flow is through an IV set having a plurality of tubing branches, as illustrated in FIG. 1. As depicted in FIG. 1, the IV set 10 generally includes a plurality of tubing branches 18, 19, 21, and 22 for providing a connection between a fluid IV bag containing a medicinal fluid (not shown) and the patient. Each of the tubing branches 18, 19, 21, and 22 may be used to deliver a different medicinal fluid in a desired quantity to the patient.

The IV set 10 may further include a connector 12 for attachment to a catheter (not shown) that may be positioned intravenously in the patient. As illustrated in FIG. 1, the IV extension set 10 may also include adapters 30, 32, 34, and 36 that allow for the administration of fluid (e.g., medicinal fluid from an IV bag or priming fluid from a syringe) into the individual tubing branches 18, 19, 21, and 22 of the IV set.

Before infusion of the medications through the IV extension set, it is desirable to prime each of the multiple tubings of the IV extension set in order to remove air from IV sets such as the IV extension set 10, which access a patient's blood flow. This is desirable for example, because air from the inside of the tubing branches may end up producing air bubbles in the medication to be delivered, thereby causing incorrect dosages of medication to be dispensed to the patient through the tubing. While this is a concern when accessing arterial blood, it is also a concern when accessing the venous side. Specifically, if air bubbles are allowed to enter a patient's blood stream while receiving the intravenous administration of fluids, the air bubbles can form an air embolism and cause serious injury to a patient.

For the majority of the adult population, the right atrium and the left atrium may be completely separated from each other so that the blood and air bubbles are moved from the right atrium, to the right ventricle, and then to the lungs where the air bubbles may be safely vented. The bubble-free blood may then be returned to the left atrium, where the blood is moved to the left ventricle and then sent throughout the body. However, in some cases, such as with infants and in a portion of the adult population, the right atrium and left atrium are not completely separated. Consequently, air bubbles travelling along with the medicinal fluid in each of the tubing branches 18, 19, 21, and 22 may be transferred to the patient and can move directly from the right atrium into the left atrium and then be dispersed throughout the body. As a result, these air bubbles may cause strokes, tissue damage, and/or death. Therefore, it is important to prevent air bubbles from entering a patient's blood stream by priming the tubing branches of the IV extension set.

In spite of the importance of removing air bubbles while priming an IV set for use in the intravenous administration of fluids, the complete removal of air bubbles can be a time consuming process. For example, due to the multiple branches of tubing in traditional IV extension sets, for example the IV extension set illustrated in FIG. 1 described below, the practitioner connects a syringe to each of the adapters 30, 32, 34, 36 of the respective tubing branches 18, 19, 21, and 22, one at a time, in order to prime each of the multiple tubing branches. Since each of the branches of tubing 18, 19, 21, and 22 of the traditional IV extension set 10 are primed individually (one at a time), the priming process can be time consuming, especially if the extension set has several branches. As a result, the overall priming process of the traditional multi-tubing IV extension set 10 may be somewhat inefficient.

The priming process using a conventional IV set such as the IV extension set 10 may also lead to contamination of the IV set by inadvertently touching a sterile end of the IV set. Typically, when the IV set 10 is primed, clamps 27 may be closed to prevent fluid from moving from a drip chamber (attached to the IV bag) through the individual tubing branches 18, 19, 21, and 22. The drip chamber, which is typically made of a clear flexible plastic, may be squeezed to draw the fluid out of the IV bag or bottle and into the drip chamber. The drip chamber may then be allowed to fill to a predetermined amount, and the clamp 27 on the respective tubing branch 18, 19, 21, and 22 connected to drip chamber and IV bag may be opened to allow fluid to flow through the individual tubings 18, 19, 21, and 22 to an end 14 of the IV set 10.

This conventional priming process, however, typically leads to the aforementioned air bubbles being trapped in the tubing branches 18, 19, 21, and 22, and which must be removed. For example, the flow of the fluid through the tubing branches 18, 19, 21, and 22 of the IV set may be turbulent and can entrap air within each of the tubes 18, 19, 21, and 22 as the boundary layer between the fluid and the tubing 18, 19, 21, and 22 is sheared. Additionally, the flow rate out of the drip chamber may be higher than the flow rate of fluid entering the drip chamber. This can cause a bubble ladder to form as air is drawn from the drip chamber into the respective tubing 18, 19, 21, and 22.

Additionally, air bubbles may be generated as drops of fluid strike the surface of the pool of fluid within the drip chamber. These air bubbles can be pulled into the tubing of the IV set from the drip chamber. This problem may be aggravated in pediatric applications where the drip orifice may be smaller which may result in increased turbulence.

To remove air bubbles from the IV set, fluid from the IV bag or bottle is allowed to flow through the tubing 18, 19, 21, and 22 while an attendant taps the tubing to encourage the air bubbles out the end of the IV set. As the fluid is allowed to flow out of the IV set to clear air bubbles from the tubing 18, 19, 21, and 22, the fluid is generally allowed to flow into a waste basket or other receptacle. During this procedure the end of the tubing may contact the waste basket or be touched by the attendant and thus, become contaminated. An additional shortcoming of this debubbling process is that it requires attention and time that could have been used to perform other tasks that may be valuable to the patient.

Another debubbling method is to directly remove air bubbles from the IV set. For example, if the IV set includes connectors, e.g., connector 25 along the length of the tubing 18, 19, 21, and 22, air bubbles may be removed at the connector 25 using a syringe.

In some examples, in order to address the difficulties of removing bubbles from an IV set, various prior art IV set designs have employed a membrane for filtering air from the fluid as it flows through the IV set. For example, oftentimes a membrane may be placed in the bottom of the drip chamber so that fluid flowing out of the drip chamber must pass through the membrane. The membrane can be configured to allow the passage of fluid while blocking the passage of air. In this way, bubbles are restricted or prevented from passing into the tubing leading to the patient. Similarly, a membrane can be included in the connector that couples the tubing to a catheter to block any air present in the tubing from passing into the patient's vasculature.

The use of air filtering membranes in these prior art IV set designs have been beneficial. However, even with the use of these membranes, various drawbacks still exist. For example, if an IV fluid bag is allowed to empty, all of the fluid within the IV set will pass through the IV set and into the patient leaving the IV set full of air. Once this occurs, the IV set will have to be re-primed to remove the air from the IV set before a new fluid bag can be administered. To avoid having to re-prime the IV set, clinicians will therefore have to be present as a fluid bag is emptying to ensure that the fluid bag can be replaced before the drip chamber empties. Also, if the clinician does not notice that air has entered into the tubing, he or she may fail to re-prime the IV set when connecting a new fluid bag. This may result in air passing into the patient once the new fluid bag is administered.

The one-time priming IV extension sets 100, 200, and 300 and associated methods of the various embodiments described herein overcome the shortcomings of traditional or conventional IV sets such as the IV extension set 10 described above. For example, various embodiments of the present disclosure are directed to providing a one-time priming IV extension set, which is configured such that a syringe having priming fluid only need be connected to one of the multiple tubing branches in order to prime all tubing branches of the extension set at once. Accordingly, all branches of tubing may be simultaneously primed, leading to a quicker, more efficient priming process. Furthermore, various embodiments of the present disclosure are directed to an IV extension set having an air stop membrane that can be included within or otherwise attached to the IV extension set to prevent air bubbles from accumulating in the multiple tubing branches of the one-time priming IV extension set. Accordingly, the IV extension sets 100, 200, and 300 of the various embodiments described herein advantageously allow for venting of air bubbles which may be present in the multiple tubing branches without the potentially disadvantageous result of contamination of the tubing occurring as described above with respect to priming the traditional or conventional IV extension sets.

Figure 2B:
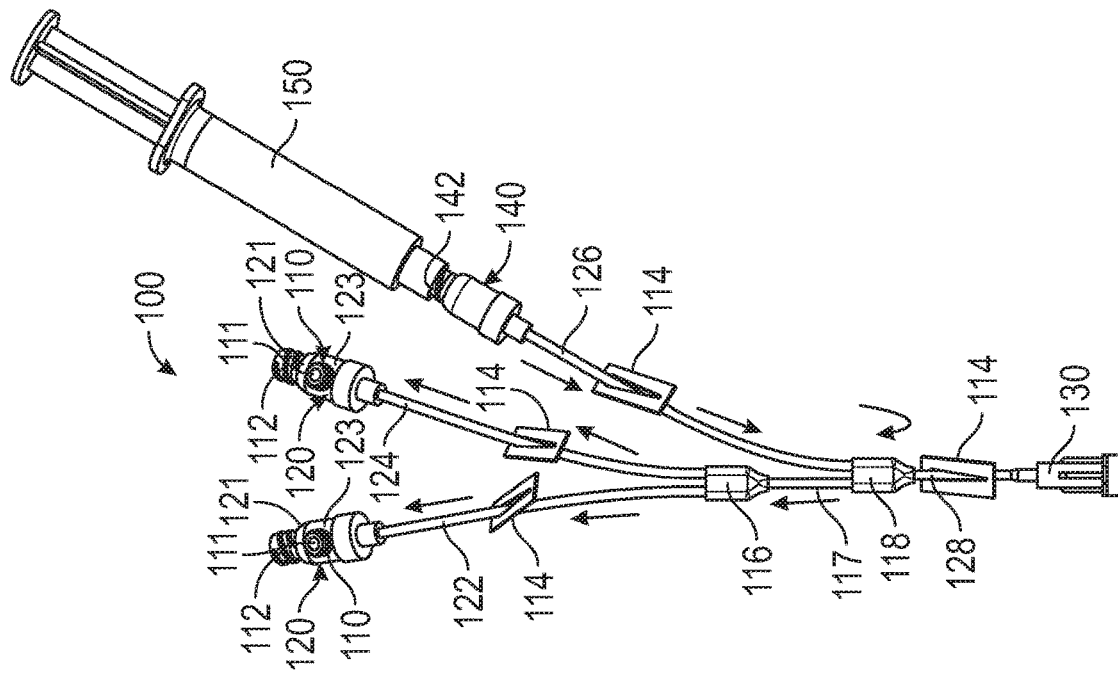
FIG. 2B illustrates a method of simultaneously priming all tubing branches of the one-time priming multi-tubing IV extension set of FIG. 2A, in accordance with some embodiments of the present disclosure.
Figure 2A:
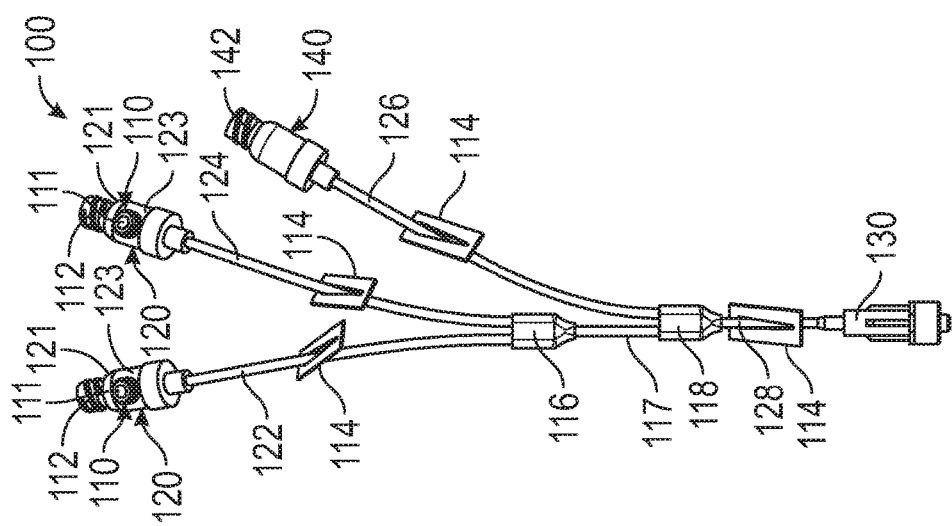
FIG. 2A illustrates a one-time priming multi-tubing IV extension set that includes a hydrophobic filter in a body of an adapter of tubing of the multiple tubing IV extension set, in accordance with some embodiments of the present disclosure.

FIG. 2A illustrates a one-time priming multi-tubing IV extension set 100 that includes a hydrophobic filter 110 in a body of an adapter 120 of secondary tubing 122, 124 of the multiple tubing IV extension set 100, in accordance with some embodiments of the present disclosure. As depicted in FIG. 2A, a multi-tubing intravenous (IV) extension set 100 for conveying at least two medicinal fluids independently from one another may include a primary inlet tubing 126 having a proximal end coupled to an adapter 140 for connection to a syringe 150 (illustrated in FIG. 2B) containing a fluid such as a priming or medicinal fluid. The primary inlet tubing 126 may further include a distal end coupled to a primary multi-tubing connector 118. The primary multi-tubing connector 118 in the various embodiments described herein serves the purpose of fluidly connecting the primary inlet tubing 126 and any additional secondary inlet tubing, e.g., inlet tubings 122 and 124 to a common outlet tubing 128 leading to the patient. In particular, in some embodiments, the outlet tubing 128 may have a proximal end coupled to an end of the primary multi-tubing connector 118 which is opposite to the end to which the primary inlet tubing 126 and the secondary inlet tubings 122 and 124 are coupled. The outlet tubing 128 may also have a distal end configured to be fluidly coupled to a vascular device for patient (not shown). Accordingly, the outlet tubing 128 may be coupled to a distal end adapter 130, for example a Luer adapter, which connects to an IV catheter (not shown) to be inserted at a target region on the body of a patient for delivery of the medicinal fluids.

FIG. 2A depicts a configuration having more than one secondary inlet tubing 122 and 124. In these embodiments, the secondary inlet tubings 122 and 124 may be fluidly connected to the primary multi-tubing connector 118 via a secondary multi-tubing connector 116. In particular, the secondary inlet tubings 122 and 124 may be fluidly coupled to an intermediate tubing 117 via the secondary multi-tubing connector 116. The intermediate tubing 117 may have a proximal end coupled to a distal end of the secondary multi-tubing connector 116 and a distal end coupled to the proximal end of the primary multi-tubing connector 118. In particular, as depicted, distal ends of the secondary inlet tubings 122 and 124 may be connected to the proximal end of the intermediate tubing 117 via the secondary multi-tubing connector 116.

However, the various embodiments described herein are not limited to the aforementioned configuration. Instead, in some embodiments, the multi-tubing IV extension set 100 may include only one secondary inlet tubing. In these embodiments, the sole secondary inlet tubing may be directly coupled to the primary multi-tubing connector 118 (i.e., without the need for a secondary multi-tubing connector 116 to be interposed therebetween) for fluid communication with the outlet tubing 128.

In accordance with various embodiments, the at least one secondary inlet tubing 122 and 124 may include, at a proximal end thereof, the adapter 120 for receiving a medicinal fluid. For example, each of the secondary inlet tubings 122 and 124 may be connected to an IV bag or a needle through the adapter 120, as previously described above. As such, the medicinal fluid may be dispensed from the IV bag or syringe to the secondary inlet tubing 122, 124 through the adapter 120. In some embodiments, each adapter 120 of the at least one secondary inlet tubing 122 and 124 has a tubular body 121 including an outer surface 123 and an inner surface defining a lumen therethrough. Thus, the adapter 120 may be in the form of a hollow tubular body 121. As depicted, the body 121 of the adapter 120 may include at least one air vent 110 disposed thereon and extending from the inner surface to the outer surface 123 of the body. The at least one air vent 110 may extend from the interior to the exterior of the body 121 so as to fluidly communicate the lumen with an exterior of the tubular body 121.

In some embodiments, a permeable membrane 111 may be disposed over or in the air vent 110 and configured to allow air to vent from the lumen of the tubular body 121 to the exterior of the tubular body 121. For example, in some embodiments, the permeable membrane 111 may be a hydrophobic membrane configured to block liquid flow while allowing the air to vent between the lumen and the exterior of the tubular body 121. As such, when the tubings 122 and 124 are primed with a priming fluid, any air existing therein may be forced out of the tubings 122 and 124, through hydrophobic membrane in the air vent 110 and out to the exterior of the tubular body 121 by the priming fluid.

In accordance with various embodiments of the present disclosure, a slide clamp 114 may be positioned on the outlet tubing 117 and configured to restrict fluid flow between the proximal and distal ends of the outlet tubing 117 when placed into a closed configuration. For example, the slide clamp 114 may be pinched or otherwise bent into the closed configuration where it causes a restriction in the outlet tubing 117 to block any fluid communication between the proximal and distal ends of the outlet tubing 117 so that priming fluid is forced to reverse direction and flow backwards (or upstream) into the at least one secondary inlet tubing 124 via the primary multi-tubing connector 118. In the embodiments illustrated in FIGS. 2A and 2B where the IV extension set 100 includes more than one secondary inlet tubing 122 and 124, the priming fluid is forced to reverse direction and flow into the secondary inlet tubings 122 and 124 via the primary multi-tubing connector 118, the intermediate tubing 117, and the secondary multi-tubing connector 116.

FIG. 2B illustrates a method of simultaneously priming all tubing branches of the one-time priming multi-tubing IV extension set of FIG. 2A, in accordance with some embodiments of the present disclosure. As depicted, the method of simultaneously (one-time) priming the primary inlet tubing 126 and the secondary inlet tubings 122 and 124 includes connecting the syringe 150 to the adapter 140 of the primary inlet tubing 126 and pinching, bending, or otherwise folding the slide clamp 114 to block fluid flow between the proximal and distal ends of the outlet tubing 128. The method further includes depressing the plunger of the syringe 150 in order to force the priming fluid, e.g., saline, from the syringe 150 into the primary inlet tubing 126. The continuous flow of priming fluid from the syringe 150 causes the priming fluid to flow through the primary multi-tubing connector 118 and into the outlet tubing 128.

Once the priming fluid reaches the restriction where the slide clamp 114 cuts off fluid communication between the proximal and distal ends of the outlet tubing 114, the priming fluid is forced to reverse direction, and flow upstream back through the primary multi-tubing connector 118 and into the plurality of secondary inlet tubings 122 and 124 via the intermediate tubing 117 and the secondary multi-tubing connector 116. As the priming fluid flows upstream into the secondary inlet tubings 122 and 124, any air existing in each of the secondary inlet tubings 122 and 124 is forced out of the secondary inlet tubings 122 and 124 by the fluid flow and exits to the exterior via the air vent 110 positioned between the lumen and the exterior of the tubular body 121. After each of the tubing branches 122, 124, and 126 have been primed with the priming fluid, the slide clamp 114 positioned on the outlet tubing 128 may then be manipulated to an open configuration, thereby restoring fluid communication between the proximal and distal ends of the outlet tubing 128. In some embodiments, the method may further include depressing the plunger of the syringe 150 further so as to flow priming fluid through the primary inlet tubing 126, the primary multi-tubing connector 118, and into the distal adapter 130 to ensure adequate priming of the outlet tubing 128 and the distal adapter 130.

Accordingly, the configuration of the IV extension set 100 described herein allows for simultaneous priming of all tubing branches 122, 124, and 126, and eliminates the need for having to connect the syringe 150 separately at each of the adapters 120 in order to separately prime each of the plurality of secondary tubings 122 and 124. By incorporating the air vent 110 on the adapters 120 positioned at the proximal ends of each of the secondary inlet tubings 122 and 124 for venting of any air present in the secondary tubings 122 and 124, the IV extension set 100 of the various embodiments described herein advantageously prevents air bubbles from being trapped in the secondary tubings 122 and 124. Accordingly, the aforementioned issues associated with conventional or traditional IV sets including but not limited to administration of incorrect dosages to patients, air bubbles forming an air embolism, which could cause serious injury to a patient, and contamination of the IV set by inadvertently touching a sterile end of the IV set, may be avoided.

FIG. 3A illustrates a one-time priming multi-tubing IV extension set 200 that includes a hydrophobic filter 215 in a venting cap 211 connected to an adapter 220 of secondary tubing 122, 124 of the multiple tubing IV extension set 200 through a venting tubing 210, in accordance with some embodiments of the present disclosure. As depicted in FIG. 3A, and similar to the embodiments of FIG. 2A, a multi-tubing intravenous (IV) extension set 200 for conveying at least two medicinal fluids independent from one another may include primary inlet tubing 126 having a proximal end coupled to an adapter 140 for connection to a syringe 150 (illustrated in FIG. 3B), which contains a fluid such as a priming or medicinal fluid. The primary inlet tubing 126 may further include a distal end coupled to a primary multi-tubing connector 118. As previously discussed with respect to FIGS. 2A and 2B, the primary multi-tubing connector 118 in the various embodiments described herein serves the purpose of fluidly connecting the primary inlet tubing 126 and any additional secondary inlet tubing, e.g., inlet tubings 122 and 124 to a common outlet tubing 128 leading to the patient. In particular, in some embodiments, the outlet tubing 128 may have a proximal end coupled to an end of the primary multi-tubing connector 118 which is opposite to the end to which the primary inlet tubing 126 and the secondary inlet tubings 122 and 124 are coupled. The outlet tubing 128 may also have a distal end configured to be fluidly coupled to a vascular device for patient (not shown). Accordingly, the outlet tubing 128 may be coupled to a distal end adapter 130, for example a Luer adapter, which connects to an IV catheter (not shown) to be inserted at a target region on the body of a patient for delivery of the medicinal fluids.

FIG. 3A depicts a configuration having more than one secondary inlet tubing 122 and 124. In these embodiments, the secondary inlet tubings 122 and 124 may be fluidly connected to the primary multi-tubing connector 118 via a secondary multi-tubing connector 116. In particular, the secondary inlet tubings 122 and 124 may be fluidly coupled to an intermediate tubing 117 via the secondary multi-tubing connector 116. The intermediate tubing 117 may have a proximal end coupled to a distal end of the secondary multi-tubing connector 116 and a distal end coupled to the proximal end of the primary multi-tubing connector 118. In particular, as depicted, distal ends of the secondary inlet tubings 122 and 124 may be connected to the proximal end of the intermediate tubing 117 via the secondary multi-tubing connector 116.

However, the various embodiments described herein are not limited to the aforementioned configuration. Instead, in some embodiments, the multi-tubing IV extension set 200 may include only one secondary inlet tubing. In these embodiments, the sole secondary inlet tubing may be directly coupled to the primary multi-tubing connector 118 for fluid communication with the outlet tubing 128.

Since the primary and secondary inlet tubings 126, 122 and 124, the primary multi-tubing connector 118, the secondary multi-tubing connector 116, and the intermediate tubing 117 as well as their connection and fluid communication with respect to each other are identical as described above with respect to the one-time priming multi-tubing IV extension set 100 of FIGS. 2A and 2B, a further detailed description thereof shall be omitted with respect to the one-time priming multi-tubing IV extension set 200.

In accordance with various embodiments, the at least one secondary inlet tubing 122 and 124 may include, at a proximal end thereof, the adapter 220 for receiving a medicinal fluid. For example, each of the secondary inlet tubings 122 and 124 may be connected to an IV bag or a needle through the adapter 220, as previously described above. As such, the medicinal fluid may be dispensed from the IV bag or syringe to the secondary inlet tubing 122, 124 through the adapter 220. In some embodiments, each adapter 220 of the at least one secondary inlet tubing 122 and 124 has a tubular body 221 including an outer surface 223 and an inner surface defining a lumen therethrough. Thus, the adapter 220 may be in the form of a hollow tubular body 221. As depicted, the body 221 of the adapter 220 may include a proximal end 212 for receiving the medicinal fluid, a distal end 214 for venting air from the at least one secondary inlet tubing 122 and 124, and an inner surface defining a lumen therethrough. Each adapter 220 may include venting tubing 210 having a proximal end 217 coupled to the distal end 214 of the adapter 220, a distal end 219, and a venting lumen 213 extending therebetween. The venting lumen 213 may be fluidly communicated with the adapter lumen (disposed on the interior of tubular body 221).

In the depicted embodiments, a venting cap 211 may be disposed at a distal end of the venting tubing 210 for fluidly communicating the venting lumen 213 with an exterior of the tubular body 221. A permeable membrane 215 may be disposed over, on, or within a lumen of the venting cap 211 to allow air to vent from the adapter lumen, through the venting lumen 213, and to the exterior of the tubular body 221. For example, in some embodiments, the permeable membrane 215 may be a hydrophobic membrane configured to block liquid flow while allowing the air to vent between the venting lumen 213 and the exterior of the tubular body 221. As such, when the secondary tubings 122 and 124 are primed with a priming fluid, any air existing therein may be forced out of the tubings 122 and 124 via the lumen of the adapter 220, into the venting lumen 213, through the hydrophobic membrane of the venting cap 211, and out to the exterior of the tubular body 221 by the priming fluid.

Similar to the various embodiments of FIGS. 2A and 2B described above, a slide clamp 114 may be positioned on the outlet tubing 117 and configured to restrict fluid flow between the proximal and distal ends of the outlet tubing 117 when placed into a closed configuration. For example, the slide clamp 114 may be pinched or otherwise bent into the closed configuration where it causes a restriction in the outlet tubing 117 to block any fluid communication between the proximal and distal ends of the outlet tubing 117 so that priming fluid is forced to reverse direction and flow into the at least one secondary inlet tubing 124 via the primary multi-tubing connector 118. In the embodiments illustrated in FIGS. 3A and 3B where the IV extension set 200 includes more than one secondary inlet tubing 122 and 124, the priming fluid is forced to reverse direction and flow into the secondary inlet tubings 122 and 124 via the primary multi-tubing connector 118, the intermediate tubing 117, and the secondary multi-tubing connector 116.

FIG. 3B illustrates a method of simultaneously priming all tubing branches 122, 124, and 126 of the one-time priming multi-tubing IV extension set 200 of FIG. 3A, in accordance with some embodiments of the present disclosure. As depicted, the method of simultaneously ("one-time") priming the primary inlet tubing 126 and the secondary inlet tubings 122 and 124 includes connecting the syringe 150 to the adapter 140 of the primary inlet tubing 126 and pinching, bending, or otherwise folding the slide clamp 114 to block fluid flow between the proximal and distal ends of the outlet tubing 128. The method further includes depressing the plunger of the syringe 150 in order to force the priming fluid, e.g., saline, from the syringe 150 into the primary inlet tubing 126. The continuous flow of priming fluid from the syringe 150 causes the priming fluid to flow through the primary multi-tubing connector 118 and into the outlet tubing 128.

Once the priming fluid reaches the restriction where the slide clamp 114 cuts off fluid communication between the proximal and distal ends of the outlet tubing 114, the priming fluid is forced to reverse direction, and flow upstream back through the primary multi-tubing connector 118 and into the plurality of secondary inlet tubings 122 and 124 via the intermediate tubing 117 and the secondary multi-tubing connector 116. As the priming fluid flows upstream into the secondary inlet tubings 122 and 124, any air existing in each of the secondary inlet tubings 122 and 124 is forced out of the secondary inlet tubings 122 and 124 by the fluid flow and exits to the exterior via the venting tubing 210 and the hydrophobic membrane 215 in the venting cap 211. After each of the tubing branches 122, 124, and 126 have been primed with the priming fluid, the slide clamp 114 positioned on the outlet tubing 128 may then be manipulated to an open configuration, thereby restoring fluid communication between the proximal and distal ends of the outlet tubing 128. In some embodiments, the method may further include depressing the plunger of the syringe 150 further so as to flow priming fluid through the primary inlet tubing 126, the primary multi-tubing connector 118, and into the distal adapter 130 to ensure adequate priming of the outlet tubing 128 and the distal adapter 130.

Accordingly, the configuration of the IV extension set 200 described herein allows for simultaneous priming of all tubing branches 122, 124, and 126, and eliminates the need for having to connect the syringe 150 separately at each of the adapters 220 in order to separately prime each of the plurality of secondary tubings 122 and 124. By incorporating the venting tubing 210 and the venting cap 211 with hydrophobic membrane at the proximal ends of the adapters 220 of each of the secondary inlet tubings 122 and 124, the IV extension set 200 of the various embodiments described herein advantageously prevents air bubbles from being trapped in the secondary tubings 122 and 124. Accordingly, the aforementioned issues associated with conventional or traditional IV sets including but not limited to administration of incorrect dosages to patients, air bubbles forming an air embolism which could cause serious injury to a patient, and contamination of the IV set by inadvertently touching a sterile end of the IV set, may be avoided.

Figure 4A:
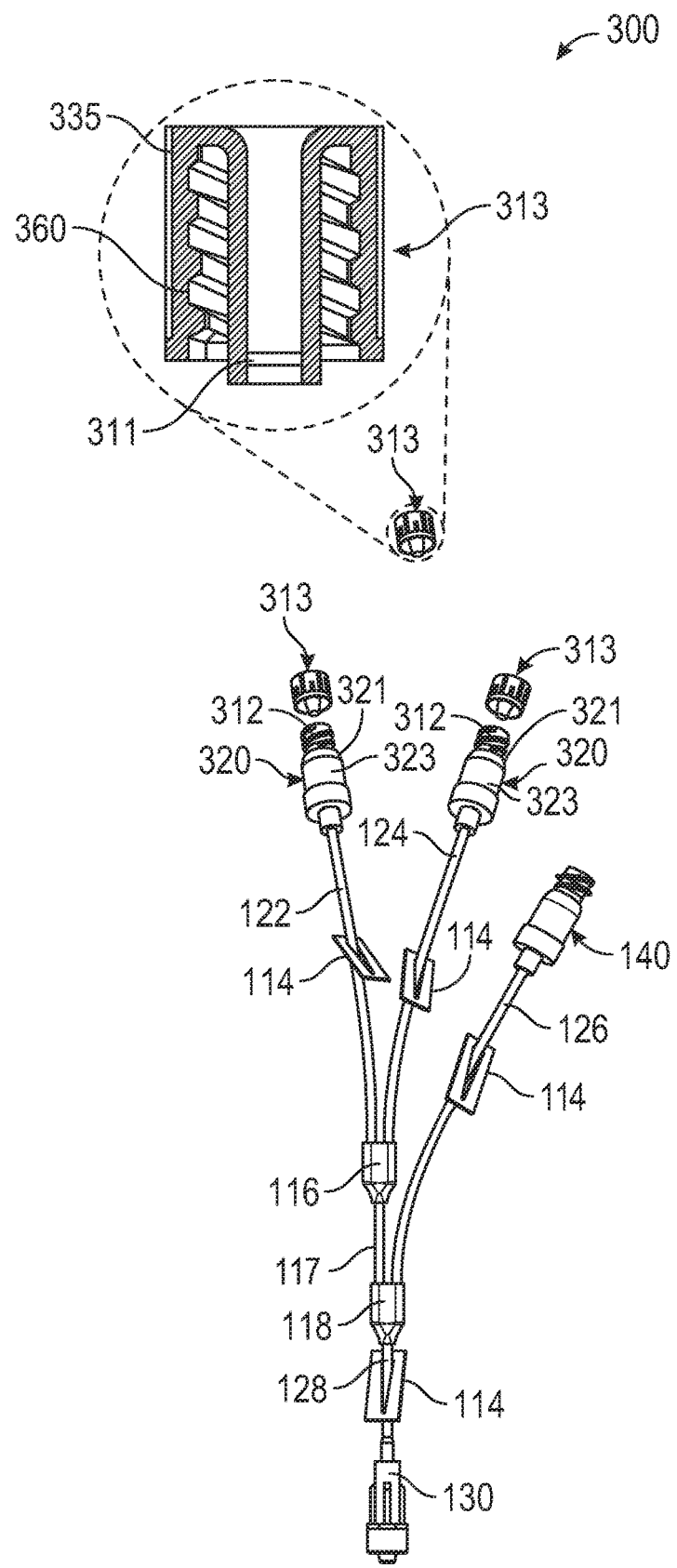
FIG. 4A illustrates a one-time priming multi-tubing IV extension set that includes a hydrophobic filter in a venting cap connected to a proximal end of an adapter of tubing of the multiple tubing IV extension set, in accordance with some embodiments of the present disclosure.

FIG. 4A illustrates a one-time priming multi-tubing IV extension set 300 that includes a hydrophobic filter 311 in a venting cap 313 connected to a proximal end of an adapter 320 of secondary tubing 122, 124 of the multiple tubing IV extension set 300, in accordance with some embodiments of the present disclosure. As depicted in FIG. 4A, and similar to the embodiments of FIG. 2A, the multi-tubing intravenous (IV) extension set 300 for conveying at least two medicinal fluids independent from one another may include a primary inlet tubing 126 having a proximal end coupled to an adapter 140 for connection to a syringe 150 (illustrated in FIG. 3B) which contains a fluid such as a priming or medicinal fluid. The primary inlet tubing 126 may further include a distal end coupled to a primary multi-tubing connector 118. As previously discussed with respect to FIGS. 2A and 2B, the primary multi-tubing connector 118 in the various embodiments described herein serves the purpose of fluidly connecting the primary inlet tubing 126 and any additional secondary inlet tubing, e.g., secondary inlet tubings 122 and 124 to a common outlet tubing 128 leading to the patient. In particular, in some embodiments, the outlet tubing 128 may have a proximal end coupled to an end of the primary multi-tubing connector 118 which is opposite to the end to which the primary inlet tubing 126 and the secondary inlet tubings 122 and 124 are coupled. The outlet tubing 128 may also have a distal end configured to be fluidly coupled to a vascular device for patient (not shown). Accordingly, the outlet tubing 128 may be coupled to a distal end adapter 130, for example a Luer adapter, which connects to an IV catheter (not shown) to be inserted at a target region on the body of a patient for delivery of the medicinal fluids.

FIG. 4A depicts a configurations having more than one secondary inlet tubing 122 and 124. In these embodiments, the secondary inlet tubings 122 and 124 may be fluidly connected to the primary multi-tubing connector 118 via a secondary multi-tubing connector 116. In particular, the secondary inlet tubings 122 and 124 may be fluidly coupled to an intermediate tubing 117 via the secondary multi-tubing connector 116. The intermediate tubing 117 may have a proximal end coupled to a distal end of the secondary multi-tubing connector 116 and a distal end coupled to the proximal end of the primary multi-tubing connector 118. In particular, as depicted, distal ends of the secondary inlet tubings 122 and 124 may be connected to the proximal end of the intermediate tubing 117 via the secondary multi-tubing connector 116.

However, the various embodiments described herein are not limited to the aforementioned configuration. Instead, in some embodiments, the multi-tubing IV extension set 200 may include only one secondary inlet tubing. In these embodiments, the sole secondary inlet tubing may be directly coupled to the primary multi-tubing connector 118 for fluid communication with the outlet tubing 128.

Since the primary and secondary inlet tubings 126, 122 and 124, the primary multi-tubing connector 118, the secondary multi-tubing connector 116, and the intermediate tubing 117 as well as their connection and fluid communication with respect to each other are identical as described above with respect to the one-time priming multi-tubing IV extension set 100 of FIGS. 2A and 2B, a further detailed description thereof shall be omitted with respect to the one-time priming multi-tubing IV extension set 300.

In accordance with various embodiments, the at least one secondary inlet tubing 122 and 124 may include, at a proximal end thereof, the adapter 320 for receiving a medicinal fluid. For example, each of the secondary inlet tubings 122 and 124 may be connected to an IV bag or a needle through the adapter 320, as previously described above. As such, the medicinal fluid may be dispensed from the IV bag or syringe to the secondary inlet tubing 122, 124 through the adapter 320. In some embodiments, each adapter 320 of the at least one secondary inlet tubing 122 and 124 has a tubular body 321 including an outer surface 323 and an inner surface defining a lumen therethrough. Thus, the adapter 320 may be in the form of a hollow tubular body 321. In some embodiments, the venting cap 313 may be formed on or otherwise integrally built into the proximal end 312 of the adapter 320 of the respective secondary inlet tubing 122 and 124. In other embodiments, the venting cap 313 may be configured to be coupled to the proximal end 312 of the adapter 320 of the respective secondary inlet tubing 122 and 124.

As depicted, the venting cap 313 may have a body 335 with a venting lumen 345 defined therethrough. The venting lumen 345 may fluidly communicate the adapter lumen with an exterior of the tubular body 321. In some embodiments, a hydrophobic filter may be a permeable membrane 311 disposed in, and coupled to an inner surface 347 of the venting cap 313 defining the venting lumen 345. The permeable membrane may be configured to allow air to vent from the secondary inlet tubings 122 and 124, through the lumen of the adapter 320, into the venting lumen 345 out to the exterior of the tubular body 320.

Similar to the embodiments of FIGS. 2A-3B, the permeable membrane 311 may be a hydrophobic membrane configured to block liquid flow between the venting lumen 345 and the exterior of the tubular body 320. As such, when the secondary tubings 122 and 124 are primed with a priming fluid, air existing therein may be forced out of the tubings 122 and 124 via the lumen of the adapter 320, into the venting lumen 345, through the hydrophobic membrane 311 of the venting cap 313, and out to the exterior of the tubular body 321 by the priming fluid.

Similar to the various embodiments of FIGS. 2A-3B described above, a slide clamp 114 may be positioned on the outlet tubing 117 and configured to restrict fluid flow between the proximal and distal ends of the outlet tubing 117 when placed into a closed configuration. For example, the slide clamp 114 may be pinched or otherwise bent into the closed configuration where it causes a restriction in the outlet tubing 117 to block any fluid communication between the proximal and distal ends of the outlet tubing 117 so that priming fluid is forced to reverse direction and flow into the at least one secondary inlet tubing 124 via the primary multi-tubing connector 118. In the embodiments illustrated in FIGS. 4A and 4B where the IV extension set 300 includes more than one secondary inlet tubing 122 and 124, the priming fluid is forced to reverse direction and flow into the secondary inlet tubings 122 and 124 via the primary multi-tubing connector 118, the intermediate tubing 117, and the secondary multi-tubing connector 116.

Figure 4B:
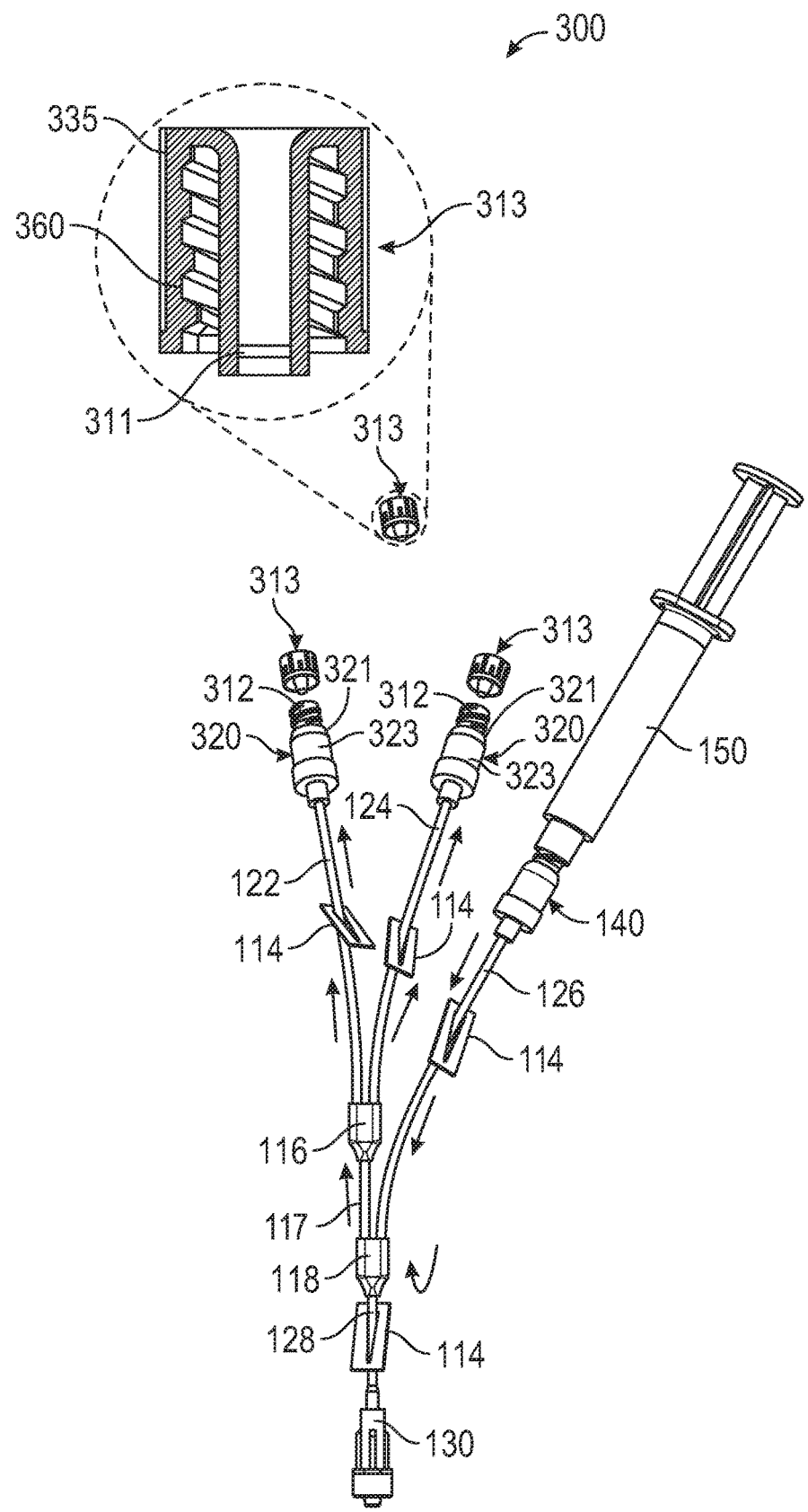
FIG. 4B illustrates a method of simultaneously priming all tubing branches of the one-time priming multi-tubing IV extension set of FIG. 4A, in accordance with some embodiments of the present disclosure.

FIG. 4B illustrates a method of simultaneously priming all tubing branches 122, 124, and 126 of the one-time priming multi-tubing IV extension set 300 of FIG. 4A, in accordance with some embodiments of the present disclosure. As depicted, the method of simultaneously ("one-time") priming the primary inlet tubing 126 and the secondary inlet tubings 122 and 124 includes connecting the syringe 150 to the adapter 140 of the primary inlet tubing 126 and pinching, bending, or otherwise folding the slide clamp 114 to block fluid flow between the proximal and distal ends of the outlet tubing 128. The method further includes depressing the plunger of the syringe 150 in order to force the priming fluid, e.g., saline, from the syringe 150 into the primary inlet tubing 126. The continuous flow of priming fluid from the syringe 150 causes the priming fluid to flow through the primary multi-tubing connector 118 and into the outlet tubing 128.

Once the priming fluid reaches the restriction where the slide clamp 114 cuts off fluid communication between the proximal and distal ends of the outlet tubing 114, the priming fluid is forced to reverse direction, and flow upstream back through the primary multi-tubing connector 118 and into the plurality of secondary inlet tubings 122 and 124 via the intermediate tubing 117 and the secondary multi-tubing connector 116. As the priming fluid flows upstream into the secondary inlet tubings 122 and 124, any air existing in each of the secondary inlet tubings 122 and 124 is forced out of the secondary inlet tubings 122 and 124 by the fluid flow and exits to the exterior via the venting lumen 345 and the hydrophobic membrane 311 in the venting cap 313. After each of the tubing branches 122, 124, and 126 have been primed with the priming fluid, the slide clamp 114 positioned on the outlet tubing 128 may then be manipulated to an open configuration, thereby restoring fluid communication between the proximal and distal ends of the outlet tubing 128. In some embodiments, the method may further include depressing the plunger of the syringe 150 further so as to flow priming fluid through the primary inlet tubing 126, the primary multi-tubing connector 118, and into the distal adapter 130 to ensure adequate priming of the outlet tubing 128 and the distal adapter 130.

Accordingly, the configuration of the IV extension set 300 described herein allows for simultaneous priming of all tubing branches 122, 124, and 126, and eliminates the need for having to connect the syringe 150 separately at each of the adapters 320 in order to separately prime each of the plurality of secondary tubings 122 and 124. By incorporating the venting cap 313 with hydrophobic membrane 311 at the proximal ends of the adapters 320 of each of the secondary inlet tubings 122 and 124, the IV extension set 300 of the various embodiments described herein advantageously prevents air bubbles from being trapped in the secondary tubings 122 and 124. Accordingly, the aforementioned issues associated with conventional or traditional IV sets including but not limited to administration of incorrect dosages to patients, air bubbles forming an air embolism which could cause serious injury to a patient, and contamination of the IV set by inadvertently touching a sterile end of the IV set, may be avoided.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A multi-tubing intravenous (IV) extension set, comprising:
an outlet tubing comprising a proximal end fluidly coupled to a primary multi-tubing connector and a distal end configured to be fluidly coupled to a vascular device for patient;
a primary inlet tubing comprising a proximal end having an adapter for connection to a syringe containing a priming or a medicinal fluid, and a distal end coupled to the primary multi-tubing connector;
at least one secondary inlet tubing comprising a proximal end having an adapter for receiving a medicinal fluid and a distal end selectively fluidly coupled to the primary multi-tubing, the adapter comprising a tubular body having a proximal end, a distal end fluidly coupled to the proximal end of the at least one secondary inlet tubing, an outer surface, an inner surface defining a lumen therethrough, and an air vent extending between the proximal and distal ends of the tubular body, and from the inner surface to the outer surface of the tubular body to fluidly communicate the lumen with the outer surface of the tubular body; and
a slide clamp positioned on the outlet tubing and configured to restrict fluid flow between the proximal and distal ends of the outlet tubing in a closed configuration to cause priming fluid flowing into the outlet tubing via the multi-tubing connector to reverse direction and flow into the at least one secondary inlet tubing via the primary multi-tubing connector.

2. The multi-tubing IV extension set of claim 1, wherein the at least one secondary inlet tubing comprises a plurality of secondary inlet tubings fluidly coupled to the primary multi-tubing connector via a secondary multi-tubing connector.

3. The multi-tubing IV extension set of claim 2, wherein each of the plurality of secondary inlet tubings have a distal end fluidly connected to the secondary multi-tubing connector.

4. The multi-tubing IV extension set of claim 2, wherein:
the secondary multi-tubing connector is fluidly coupled to the primary multi-tubing connector via an intermediate tubing; and
the intermediate tubing comprises:
a proximal end fluidly connected to a distal end of the secondary multi-tubing connector; and
a distal end fluidly coupled to the proximal end of the primary multi-tubing connector.

5. The multi-tubing IV extension set of claim 1, wherein the secondary inlet tubing comprises a single inlet tubing directly fluidly coupled to the primary multi-tubing connector.

6. The multi-tubing IV extension set of claim 1, further comprising a permeable membrane disposed over the air vent, the permeable membrane configured to allow air to vent from the lumen to the exterior of the tubular body.

7. The multi-tubing IV extension set of claim 6, wherein the permeable membrane comprises a hydrophobic membrane configured to block liquid flow between the lumen and the exterior of the tubular body.

8. The multi-tubing IV extension set of claim 1, further comprising a venting cap disposed on the proximal end of the adapter of the at least one secondary inlet tubing, wherein the venting cap has a body with a venting lumen defined therethrough, the venting lumen fluidly communicating the adapter lumen with an exterior of the tubular body.

9. The multi-tubing IV extension set of claim 8, further comprising a permeable membrane disposed over, on, or within a lumen of the venting cap, the permeable membrane configured to allow air to vent from the adapter lumen, through the venting lumen, and to the exterior of the tubular body.

10. The multi-tubing IV extension set of claim 8, further comprising a permeable membrane disposed in, and coupled to an inner surface of the venting cap defining the venting lumen, the permeable membrane configured to allow air to vent from the lumen to the exterior of the tubular body.

11. The multi-tubing IV extension set of claim 10, wherein the permeable membrane comprises a hydrophobic membrane configured to block liquid flow between the lumen and the exterior of the tubular body.

12. A method of simultaneously priming a plurality of tubing branches of a multi-tubing intravenous (IV) extension set having a primary inlet tubing fluidly coupled to a primary multi-tubing connector, at least one secondary inlet tubing fluidly coupled to the primary multi-tubing connector, and an outlet tubing fluidly coupling the primary multi-tubing connector to a vascular device, the method comprising:

connecting a syringe to adapter of the primary inlet tubing:

pinching, bending, or otherwise folding a slide clamp positioned on the outlet tubing to block fluid flow between the proximal and distal ends of the outlet tubing;

depressing a plunger of the syringe in order to force priming fluid from the syringe downstream through the primary inlet tubing and into the outlet tubing via the primary multi-tubing connector;

reversing flow of the priming fluid to flow back upstream through the primary multi-tubing connector and into the at least one secondary inlet tubing; and venting air existing in the at least one secondary inlet tubing out of the at least one secondary inlet tubing and through an air vent of an adapter fluidly coupled to the at least one secondary inlet tubing by flowing the priming fluid therethrough, wherein the adapter comprises a proximal end, a distal end, and an air vent extending between the proximal and distal ends of the adapter, and from the inner surface to the outer surface of the adapter to fluidly communicate the lumen with the outer surface of the adapter.

13. The method of claim 12, wherein:

the reversing flow of the priming fluid comprises positioning a slide clamp on the outlet tubing and placing the slide clamp in a closed configuration to form a restriction in the outlet tubing; and upon reaching the restriction, flow of the priming fluid is diverted from the downstream direction to the upstream direction towards the at least one secondary inlet tubing.

14. The method of claim 13, wherein each secondary inlet tubing comprises a plurality of secondary inlet tubings fluidly coupled to the primary multi-tubing connector via a secondary multi-tubing connector and an intermediate tubing, the venting air existing in the at least one secondary inlet tubing comprising venting air existing in plurality of secondary inlet tubings by simultaneously the flowing priming through the main and secondary inlet tubings.

15. The method of claim 14, wherein each secondary inlet tubing comprises an adapter having at least one air vent extending from an inner lumen to an outer surface of the adapter, the venting air existing in the plurality of secondary inlet tubings comprising simultaneously flowing the priming fluid upstream through the secondary inlet tubings to force the air to an exterior of the secondary inlet tubings via the inner lumen and a hydrophobic filter of the air vent.

16. The method of claim 14, wherein each secondary inlet tubing comprises an adapter having a venting tubing with a venting lumen fluidly communicated with the respective secondary inlet tubing, and a venting cap fluidly coupled at a distal end of the venting tubing, the venting air existing in the plurality of the secondary inlet tubings comprising simultaneously flowing the priming fluid upstream through the secondary inlet tubings to force the air to an exterior of the secondary inlet tubings via the venting lumen and a hydrophobic filter of the venting cap.

17. The method of claim 14, wherein each secondary inlet tubing comprises an adapter including a venting cap having a venting lumen fluidly communicated with the respective secondary inlet tubing a hydrophobic filter disposed in the venting lumen, the venting air existing in the plurality of the secondary inlet tubings to force the air to an exterior of the secondary inlet tubings via the venting lumen and a hydrophobic filter of the venting cap.

18. A multi-tubing intravenous (IV) extension set, comprising:

an outlet tubing comprising a proximal end fluidly coupled to a primary multi-tubing connector and a distal end configured to be fluidly coupled to a vascular device for patient;

a primary inlet tubing comprising a proximal end having an adapter for connection to a syringe containing a priming or a medicinal fluid, and a distal end coupled to the primary multi-tubing connector;

at least one secondary inlet tubing comprising a proximal end and a distal end, wherein the distal end of the at least one secondary inlet tubing is selectively fluidly coupled to the proximal end of the primary multi-tubing;

an adapter comprising a proximal end for receiving the medicinal fluid, a distal end coupled to the at least one secondary inlet tubing, an inner surface defining a lumen through the adapter, a venting tubing having a proximal end coupled to the distal end of the adapter, a distal end, and a venting lumen extending therebetween, the venting lumen being fluidly communicated with the adapter lumen; and a slide clamp positioned on the outlet tubing and configured to restrict fluid flow between the proximal and distal ends of the outlet tubing in a closed configuration to cause priming fluid flowing into the outlet tubing via the multi-tubing connector to reverse direction and flow into the at least one secondary inlet tubing via the primary multi-tubing connector.

19. The multi-tubing IV extension set of claim 18, wherein the permeable membrane comprises a hydrophobic membrane configured to block liquid flow while allowing the air to vent between the venting lumen and the exterior of the tubular body.

* * * * *